United States Patent [19]

Moldawer et al.

[11] Patent Number: 4,542,017
[45] Date of Patent: Sep. 17, 1985

[54] TREATMENT OF PROTEIN MALNOURISHED BACTERIALLY INFECTED HUMANS WITH LEM

[76] Inventors: Lyle L. Moldawer, 1 E. Quinobequin Rd., Waban, Mass. 02169; George L. Blackburn, 100 Memorial Dr., Cambridge, Mass. 02142; Bruce R. Bistrian, 189 Argilla Rd., Ipswich, Mass. 01938

[21] Appl. No.: 448,183

[22] Filed: Dec. 9, 1982

[51] Int. Cl.[4] .............................................. A61K 35/14
[52] U.S. Cl. ...................................... 424/101; 424/88
[58] Field of Search .................................. 424/101, 88

[56] References Cited

PUBLICATIONS

Dinarello et al.—Chem. Abst., vol. 95 (1981), p. 113,212a.
Chem. Abst., General Subject Index, 10th Collective, vol. 86–95 (1977–1981), p. 13929GS.
L. Hoffman–Goetz and M. J. Kluger, "Protein Deprivation: Its Effects on Fever and Plasma Iron During Bacterial Infection in Rabbits," *J. Physiol.*, 295, (1979), pp. 419–430.
L. Hoffman–Goetz and M. J. Kluger, "Protein Deficiency: Its Effects on Body Temperature in Health and Disease States," *Am. J. Clin. Nutrition*, 32, (Jul. 1979), pp. 1423–1427.
L. Hoffman–Goetz, et al., "Febrile and Plasma Iron Response of Rabbits Injected with Endogenous Pyrogen from Malnourished Patients," *Am. J. Clin. Nutr.*, 34, (Jun. 1981), pp. 1109–1116.
R. A. Keenan, et al., "An Altered Response by Peripheral Leukocytes to Synthesize or Release Leukocyte Endogenous Mediator in Critically Ill, Protein-Malnourished Patients," *J. Lab. and Clin. Med.*, 100, (Dec. 1982), pp. 844–857.
K. B. Harvey, et al., "Biological Measures for the Formulation of a Hospital Prognostic Index," *Am. J. Clin. Nutr.*, 34, (Oct. 1981), pp. 2013–2022.
R. F. Kampschmidt and L. A. Pulliam, "Stimulation of Antimicrobial Activity in the Rat with Leukocytic Endogenous Mediator," *J. Reticuloendothelial Soc.*, 17, (Mar. 1975), pp. 162–169.
M. C. Powanda and W. R. Beisel, "Hypothesis: Leukocyte Endogenous Mediator/Endogenous Pyrogen/-Lymphocyte-Activating Factor Modulates the Development of Nonspecific and Specific Immunity and Affects Nutritional Status," *Am. J. Clin. Nutr.*, 35, (Apr. 1982), pp. 762–768.
G. H. A. Clowes, Jr., et al., "Muscle Proteolysis Induced by a Circulating Peptide in Patients with Sepsis or Trauma," *N.E. J. Med.*, 308, (Mar. 10, 1983), pp. 545–552.
V. Baracos, et al., "Stimulation of Muscle Protein Degradation and Prostaglandin $E_2$ Release by Leukocyte Pyrogen (Interleukin-1)," *N.E. J. Med.*, 308, (Mar. 10, 1983), pp. 553–558.
W. R. Beisel, "Mediators of Fever and Muscle Proteolysis," *N.E. J. Med.*, 308, (Mar. 10, 1983), pp. 586–587.

*Primary Examiner*—Sam Rosen
*Attorney, Agent, or Firm*—Donald Brown

[57] ABSTRACT

Exogenous LEM (Leukocyte Endogenous Mediator, also referred to as endogenous pyrogen) is parenterally administered to humans who are protein malnourished and are infected with bacteria, in order to preinitiate and then maintain the normal metabolic responses to the tissue damage occurring during infection, and thereby promote the normal metabolic response by the human.

4 Claims, No Drawings

TREATMENT OF PROTEIN MALNOURISHED BACTERIALLY INFECTED HUMANS WITH LEM

BACKGROUND OF THE DISCLOSURE

Acute bacterial infections in the human body cause many effects including severe tissue damage. It has been found that normal patients who have bacterial infections (either gram negative or positve) should normally produce a series of nonspecific metabolic responses to the invading pathogen. These metabolic responses tend to alleviate the symptoms associated with such tissue damage and in particular enhance the body's ability to limit tissue damage and reduce the likelihood of the patient ultimately succumbing to the pathogen.

There are large numbers of people who become infected but have substantially diminished capability to produce the normal metabolic responses to such tissue damage. These individuals are generally those who are protein malnourished and surprisingly constitute a substantial portion of those patients who become infected. Protein malnourished patients are normally considered as those having a serum albumin level of less than about 3.2 gm/dl.

With the present invention it is now possible to provide parenteral therapy to such humans (patients), to first initiate and then maintain the normal metabolic response which would ordinarily be set off in normal humans to promote the human's ability to overcome invading bacteria. In this invention a sufficient amount of LEM (leukocyte endogenous mediator, also sometimes known as leukocyte pyrogen, endogenous pyrogen, lymphocyte activating factor or Interleukin I) is parenterally administered to raise the body temperature of a human above normal and usually at least about 1° C. With this invention it is now possible to marshall the human's ability to fight off, by stimulating the human's metabolism, tissue damage and to reduce increased morbidity and mortality which are often associated with bacterial infections in protein malnourished human patients.

LEM (endogenous pyrogen) is a well known material. It may be classified as a hormone in that it appears to be a substance which is produced in one region of the body and transported to another region where it induces a specific bodily response. The isolation and various experiments with same have been reported in the scientific literature for many years. See:

Kampschmidt, R. F., Upchurch, H. F., Eddington, C. L. Pulliam, L. A. Multiple biological activities of a partially purified leukocytic endogenous mediator. Am. J. Physiol., 224:530, 1973;

Kampschmidt, R. F. Leukocytic endogenous mediator. J. Reticuloendothel Soc., 23:287, 1978;

Dinarello, C. A., Goldin, N. P., Wolff, S. M. Demonstration and characterization of two distinct human leukocyte pyrogens. J. Exp. Med., 139:1369, 1974;

Bodel, P. Studies on the mechanism of endogenous pyrogen production. III. Human blood monocytes. J. Exp. Med., 140:954, 1974;

Kaiser, H. K., Wood, W. B., Jr. Studies on the pathogenesis of fever: Role of endogenous pyrogen by polymorphonuclear leukocytes. J. Exp. Med., 136:944, 1971;

Kampschmidt, R. F., Pulliam, L. A., Upchurch, H. F. Sources of leukocytic endogenous mediator in the rat. Proc. Soc. Exp. Biol. Med., 144:882, 1973;

Bodel, P., Miller, H. Pyrogen from mouse macrophages causes fever in mice. Proc. Soc. Exp. Biol. Med., 151:93, 1976;

Kampschmidt, R. F., Upchurch, H. F. Lowering of plasma iron concentrations in the rat with leukocytic extracts. Am. J. Physiol., 216:1287, 1969;

Kampschmidt, R. F., Upchurch, H. F. The effect of endogenous pyrogen on the plasma zinc concentration of the rat. Proc. Soc. Exp. Biol. Med., 134:1150, 1970;

Bornstein, D. L., Bredenberg, C., Wood, B. W. Studies on the pathogenesis of fever XI. Quantitative features of the febrile response to leukocytic pyrogen. J. Exp. Med. 117:349, 1963;

Cheuk, S. F., Hahn, H. H., Moore, D. M., Krause, D. N., Tomasulo, P. A., Wood, W. B., Jr. Studies on the pathogenesis of fever. XX. Suppression and regeneration of pyrogen-producing capacity of exudate granulocytes. J. Exp. Med., 132:127, 1970;

Wannemacher, R. W., Jr., Pekarek, R. S., Beisel, W. R. Mediator of hepatic amino acid flux in infected rats. Proc. Soc. Exp. Biol. Med., 139:128, 1972;

Eddington, C. L., Upchurch, H. F., Kampschmidt, R. F. Effect of extracts from rabbit leukocytes on levels of acute phase globulins in rat serum. Proc. Soc. Exp. Biol. in Med., 126:159, 1971;

Kampschmidt, R. F., Upchurch, H. F. Possible involvement of leukocytic endogenous mediator in granulopoiesis. Proc. Soc. Exp. Biol. Med., 155:89, 1977;

George, D. T., Abeles, F. B., Mapes, C. A., Sobocinski, P. Z., Zenser, T. V., Powanda, M. C. Effect of leukocytic endogenous mediators on endocrine pancreas secretory responses. Am. J. Physiol., 223:E240, 1977;

Murphy, P. A., Simon, P. L., Willoughby, W. F. Endogenous pyrogens made by rabbit peritoneal exudate cells are identical with lymphycyte-activating factors made by rabbit alveolar macrophages. J. Immunol., 124:2498, 1980;

Rosenwasser, L. J., Dinarello, C. A., Rosenthal, A. S. Adherent cell function in murine T-lymphocyte antigen recognition. IV. Enhancement of murine T-cell antigen recognition by human leukocytic pyrogen. J. Exp. Med., 150:709, 1979; and Moore, R. N., Oppenheim, J. J., Farrar, J. J., Carter, C. S., Jr., Waheed, A., Shadduck, R. K. Production of lymphocyte-activating factor (Interleukin 1) by macrophages activated with colony-stimulating factors. J. Immunol., 125:1302, 1980.

BRIEF STATEMENT OF THE INVENTION

This invention is particularly directed to the parenteral administration of LEM, preferably human LEM, to a protein malnourished human who has a bacterial infection, e.g, Pseudomonas, Bacteroides, Klebsiella, E. coli, Staphylococcus aureus, Streptococcus pneumoniae. It should be understood that animal produced LEM may be used in place of human LEM, or ultimately LEM produced genetically or synthetically as these technologies develop. The LEM administered should be sufficient to generate a rise in human body temperature of preferably at least about 1° C. The LEM will normally be administered during the period in which the human patient is infected to maintain elevated body temperature. In this manner, the patient's metabolism is stimulated by LEM to generate a fever and at the same time to cause one or more of the following to be mediated in the human's body:

1. reduced plasma concentrations of zinc and iron 2. increased plasma concentration of copper as ceruloplasmin
3. increased hepatic synthesis of the 'acute-phase' proteins:
   $\alpha_1$-antitrypsin,
   $\alpha_1$-acid glycoprotein,
   $\alpha_2$-macroglobulin,
   haptoglobin,
   C-reactive protein.
4. increased serum concentrations of insulin and glucagon
5. increased muscle protein breakdown and net catabolism
6. increased liver weight and protein content
7. redistribution of host protein from somatic to visceral tissues
8. increased blood glucose levels
9. reduced fasting ketonemia
10. increased prostaglandin production
11. increased lymphocyte proliferation in response to antigens
12. increased neutrophil lysozyme production
13. increased neutrophil superoxide production
14. increased production of colony stimulating factor (macrophage)
15. increased granulocytosis
16. increased release of immature granulocytes (band forms) from bone marrow The metabolic functions, 1 through 16 listed above, are intimately beneficially involved with the body's ability to fight bacterial infections.

Thus with this invention the protein malnourished patient who normally is unable to generate sufficient endogenous LEM is able to better overcome, i.e. survive, bacterial infections.

In order to use this invention the LEM may be parenterally administered, e.g., by injection such as intravenous, subcutaneous or intramuscular, or intravenous drip. The dosage would obviously vary; however, it is preferred that the dosage administered produce a prolonged 1° C. rise in patient (human) body temperature (e.g., one to four hours each six hour bolus IV administration). Preferably, the dosage of LEM is about 1–40 nanograms per kg of human body weight, and most preferably, 3–20 nanograms per kg of human body weight for a single dose injection every six hours. An intravenous drip for 24 hours would contain 4–150 nanograms per kg of human body weight per hour given continuously. However, it should be understood that additional LEM may be administered to further elevate body temperature 2° to 3° C. over normal depending upon the human.

As used herein, "bacterial infection" refers to, but is not limited by, the presence of bacteremia (either gram negative or positive) proven by peripheral blood culture, an identifiable intra-abdominal or intra-thoracic abscess, bacterial endocarditis, pulmonary atelectasis or pneumonia.

As used herein it should be understood that the term LEM is intended to include pharmaceutically acceptable salts, e.g., acid-addition salts thereof, such as for example, phosphates, chloride, acetic acid, and salts of bases such as for example barium hydroxide and sodium hydroxide.

The invention will now be illustrated with reference to the following examples. In the examples all temperatures are in degrees centigrade.

EXAMPLE 1

Preparation of Human LEM

All glassware, materials, and reagents used in the procedure are sterile and endotoxin-free. 500 ml of anticoagulated (citrate) venous human blood is allowed to sediment on a Ficoll-Hypaque gradient (Pharmacia, Inc., Stockholm, Sweden) at 9° C. The monocyte-rich fraction is then separated from erythrocytes and centrifuged at 900×g for 10 minutes. After removal of any remaining erythrocytes by brief exposure to hypotonic saline, the monocytes are washed with saline and 5% dextrose and then resuspended in Hanks' balanced salt solution containing 10 U/ml of sodium heparin, 150 mg/dl glucose, and 1000 U/ml of penicillin G (sodium salt). Approximately $1 \times 10^8$ monocytes are stimulated to produce LEM by incubation with $3 \times 10^9$ heat-killed *Staphylococcus albus* for 18 hours.

Briefly, *Staphylococcus albus* ($3 \times 10^9$ colony forming units) is added to phosphate buffered saline (pH 7.4) and heated to 100° C. for 30 minutes. The heat-killed bacteria are cooled to 37° C. and placed in a shaking water bath with the monocytes at a ratio of 30 heat-killed bacteria to one monocyte and the solution incubated at 37° for 18 hours.

After the 18 hour incubation, the bacteria and cells are removed by centrifugation at 3600×g for 30 min and the supernatant passed through a 0.45 micron filter (Millipore Corp., Bedford, Mass.) Aliquots of LEM are tested prior to purification for (1) endotoxin contamination with Limulus lysate assay (Pyrotell; Associates of Cape Cod, Falmouth, Mass.) and (2) bacterial contamination by culturing in thioglycollate medium at 37° C. for 48 hr.

Purification of Human LEM

The supernatant containing LEM is then diluted in ten volumes of sterile and pyrogen-free phosphate buffered saline (pH 7.4) and subjected to ultrafiltration across an anisotropic membrane fractioning at molecular weights of approximately 35,000–50,000 daltons (Amicon, Danvers, Mass.). The less than 50,000 dalton fraction containing LEM is dialyzed against a Tris buffer (pH 8.1) at 4° C. for 12 hours and is then applied to a DEAE-cellulose ion-exchange column (DEAE-cellulose, DE-52, Whatman Ltd., London, England). The LEM is eluted with a sodium chloride gradient in the first ten to twenty fractions at 3–5 mmhols. The resulting LEM is concentrated by lyophilization and is again tested for pyrogenicity and sterility by Limulus lysate assay and evidence of bacterial growth, respectively.

EXAMPLE 2

Hypodermic Solutions for IV Bolus

The solution is compounded from the following:

| LEM | 1000 nanograms |
|---|---|
| Sodium chloride | 5 parts by volume |
| Double-distilled water q.s. ad | 500 parts by volume |
| Human serum albumin | 5 parts by volume |

The active ingredient LEM, human serum albumin and sodium chloride are dissolved in the distilled water; the solution is sterilized and made free from suspended particles by being filtered (0.22 micron), and is filled into a 5 cc-ampule which is sealed. The human serum albumin is added only to prevent adhesion of the LEM to glass and subsequently to plastic syringes and/or tubing. The contents of the ampule are an injectable dosage unit composition. For continuous intravenous administration, four vials of the solution of Example 2 are injected each hour into a 0.5% saline solution (drip) normally used for IV administration.

EXAMPLE 3

A protein malnourished patient (human) 70 kg man with an abdominal abscess and gram negative bacteremia (Klebsiella) infection is administered by continuous IV drip 4000 nanograms of LEM per hour in 0.5% saline solutions for a period of three days. The human is monitored for temperature elevation and the IV drip adjusted to maintain human body temperature to about 1° C. over normal.

The amount of active ingredient in these illustrative examples may be varied to achieve the dosage unit range set forth above, and the amounts and nature of the inert pharmaceutical carrier ingredients may be varied to meet particular patient requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

What is claimed is:

1. The method of stimulating metabolic function comprising treating a protein mainourished human who has a serum albumin less than about 3.2 gm/dl and who is bacterially infected by parenterally admistering to said human during said infection a sufficinet amount of LEM to supplement LEM being endogenously produced by said human and to raise the body temperature of the human above normal during at least some of the time the human is infected.

2. The method of claim 1 in which the LEM is administered intravenously.

3. The method of claim 1 in which the LEM is administered in the form of a sterile injectable preparation or sterile intravenous drip.

4. The method of claim 1 in which the amount of LEM administered is sufficient to raise the human's body temperature at least about one degree centigrade.

* * * * *